United States Patent [19]
Vander Velde

[11] Patent Number: 5,365,779
[45] Date of Patent: Nov. 22, 1994

[54] CORROSION CONDITION EVALUATION AND CORROSION PROTECTION OF UNBONDED POST-TENSION CABLES IN CONCRETE STRUCTURES

[76] Inventor: Henry Vander Velde, c/o 2199 Carling Avenue, Ottawa, Ontario, Canada, K2B 7E8

[21] Appl. No.: 45,720

[22] Filed: Apr. 14, 1993

[51] Int. Cl.⁵ .......................................... G01N 17/00
[52] U.S. Cl. .................................... 73/86; 73/803.83
[58] Field of Search ...... 73/24.04, 25.04, 29.01–29.05, 73/73, 86, 864.81, 863.81, 863.83, 863.31, 863.86, 864.81; 422/7, 9, 10, 14; 405/239; 52/223.6, 223.1, 310

[56] References Cited

U.S. PATENT DOCUMENTS

| | | | |
|---|---|---|---|
| 1,845,247 | 2/1932 | Davidson | 73/29.04 |
| 2,429,474 | 10/1947 | McMahon | 73/29.04 |
| 3,778,948 | 12/1973 | Berthier | 52/310 |
| 4,506,540 | 3/1985 | Marsh | 73/29.05 |
| 4,515,751 | 5/1985 | Krieg, Jr. | 73/863.86 |

FOREIGN PATENT DOCUMENTS

| | | | |
|---|---|---|---|
| 520472 | 12/1992 | European Pat. Off. | 73/73 |
| 2224852 | 5/1990 | United Kingdom | 73/86 |
| 8706958 | 11/1987 | WIPO | 422/9 |

*Primary Examiner*—Robert Raevis
*Attorney, Agent, or Firm*—Antonelli, Terry, Stout & Kraus

[57] ABSTRACT

There is disclosed a method and apparatus for the corrosion condition evaluation of unbonded prestressing elements in post-tension concrete structures. The method involves locating a prestressing element in the structure and providing at least two openings in the structure at positions along the length of the element. One of the openings is an inlet port and the other is an outlet port, each of the ports permitting communication with the gaseous environment within a conduit surrounding the prestressing element. The gaseous environment is accessed through the outlet port by extracting a sample of gas therethrough. The sample is then measured to determine its humidity and thereby evaluate the corrosion condition of the prestressing element between the inlet port and the outlet port. A method and apparatus is also provided for the on-site corrosion protection of unbonded prestressing elements whereby the gaseous environments within the conduits are cyclically pressurized with a dry gas. The protection method may also include programmable control of the dry gas pressurization and feedback of the humidity levels in the conduits for adjusting the parameters of cyclical pressurization so as to maintain a predetermined maximum humidity value in the gaseous environments associated with the prestressing elements of the structure.

64 Claims, 6 Drawing Sheets

CORROSION CONDITION EVALUATION AND CORROSION PROTECTION OF UNBONDED POST-TENSION CABLES IN CONCRETE STRUCTURES

FIELD OF THE INVENTION

The present invention relates generally to the field of post-tension concrete structures, and more particularly, to a method and apparatus for the on-site non-destructive condition evaluation and protection of unbonded prestressing elements susceptible to corrosion in such concrete structures.

BACKGROUND OF THE INVENTION

It is well-known in civil engineering practice to employ prestressing steel elements to reinforce concrete structures such as buildings, bridges, graded slabs, pavements and the like. In a post-tension concrete structure, the prestressing steel elements are disposed in a desired array prior to concrete pouring. Once a concrete member has been poured and has sufficiently cured, the prestressing elements contained within it are tensioned, and a prestressing force is thereby transmitted to the structure by means of mechanical anchorages provided at the ends of the elements and secured to the concrete member.

In an unbonded post-tension structure, the prestressing steel elements are intended on a permanent basis to move freely relative to the concrete substrate in which they are placed. Prestressing steel elements in unbonded structures may typically be found in the form of strands, cables, wires or bars. To prevent such prestressing steel elements from bonding to the concrete, they are typically enclosed in a conduit means such as a sheath of plastic or metallic tubing. In addition, the prestressing elements are usually covered with a corrosion-protective coating, which may be in the form of corrosion inhibiting greases or other coatings such as bitumastics, wax, epoxy or zinc.

It has been estimated that there exists more than 2,000,000,000 sq. ft. (185,000,000 m$^2$) of unbonded post-tension structures in the United States and Canada, with a large proportion of this construction being represented by parking structures. This may be attributed to some of the recognized or perceived advantages associated with unbonded post-tensioning, namely the attainment of long span designs, relatively shallow slab depths and improved crack control. However, despite these advantages, it has been found in practice that unbonded post-tension concrete structures have been prone to corrosion and failure of the prestressing steel elements.

Entrainment of water and corrosive contaminants within a post-tensioned concrete substrate can occur as a result of a number of design and construction defects such as inadequate concrete cover, poor-quality concrete, concrete cracking, pour concrete surface sealing practices and inadequate end anchorage protection of the prestressing elements. A prestressing element with a discontinuous grease coating, poor or defective quality grease or a loose fitting sheath will result in such entrained water and chemical contaminants coming into direct and prolonged contact with the prestressing element, thereby rendering it susceptible to corrosion.

The susceptibility of unbonded prestressing elements to corrosion may have serious effects for the long term durability and structural soundness of post-tension concrete structures. For instance, failure of a prestressing element due to severe enough corrosion may lead to eruption of the prestressing elements through the concrete cover or may even cause the tensioned prestressing elements to suddenly rupture and eject out of the structure through the end anchorages of the elements. It will be readily appreciated that both of these forms of projection of prestressing elements from the concrete structure can pose serious safety hazards. For instance, when a ruptured prestressing cable erupts through its concrete cover, it may do so with an explosive force, thereby having the potential to cause serious personal injury and property damage.

Moreover, where enough prestressing elements in a given concrete member have failed, structural deficiency may result if such unsound or disactivated prestressing elements are not located and repaired in a timely manner. Those skilled in this art will readily appreciate that since prestressing elements in an unbonded structure are only secured at their end anchorages, a single failure location along the entire length of a prestressing element will be sufficient to render the entire element ineffective for providing structural integrity. As well, any significant proportion of damage to the prestressing elements in any one area of a post-tension structure may have important consequences on the load-carrying or load-bearing capacity of the structure.

As mentioned previously, the use of post-tension structures has been prevalent in automobile parkades. In some of these structures, the concrete cover is exposed to the outside elements and in others, de-icing agents containing chlorides routinely come into contact with the concrete cover. Although the prestressing elements of the parkade structures may have been originally designed and intended to be protected from corrosion by a grease or other corrosion inhibiting coating applied to the prestressing elements at the time they are installed into their sheaths, such coatings have been found on occasion to be incomplete over the length of the element. In other instances, the coatings may emulsify or become dispersed over time by water infiltration or may otherwise be rendered ineffective. As well, even in cases where the concrete cover was initially treated to prevent water infiltration, poor maintenance or surface erosion caused by snow removing operations may subsequently render the concrete permeable to water. In such cases, infiltration of water into the concrete substrate, which may moreover contain chlorides from de-icing agents, may induce surface pitting, stress corrosion cracking and hydrogen embrittlement of the steel prestressing elements.

Where the rehabilitation of a post-tension structure calls for replacement of its prestressing elements, such repair work may result in an expense of several million dollars for a multi-storey structure containing 2,000 to 3,000 prestressing cables. However, in some cases, such an extensive degree of damage may have been caused to a post-tension structure that repair and rehabilitation of the original prestressing array is no longer technically nor economically feasible. It may therefore be appreciated that there exists a need for non-destructive methods of evaluating the corrosion condition of prestressing arrays and of protecting them from continued corrosion.

Currently, there does not appear to be a reliable, relatively inexpensive method for evaluating the condition of unbonded prestressing elements which are in service and therefore tensioned within a concrete substrate. One known method of evaluating the condition of prestressing elements is to extract a statistically relevant portion of the prestressing elements in a given structure and inspect them visually or by known instrumental testing methods. This method may also be coupled with an exploratory excavation into the concrete substrate to expose a desired additional number of prestressing elements for on-site visual examination. Based on such a method, it may be possible to statistically determine the degree of deterioration for the entire structure and take corrective measures to prevent or retard corrosion. However, not only is this approach costly, but it also requires a high degree of professional engineering judgment.

Another known method for the on-site evaluation of a prestressing cable in service involves applying a localized vacuum over the end anchorages of the prestressing element and observing both the level and rate of decay of the maximum vacuum pressure obtained. Such a method can be used to obtain an indication of the concrete plug joint tightness and relative porosity of the concrete in the vicinity of the end anchorage plug of a prestressing cable. This particular method cannot therefore be used to evaluate the condition of a cable along longitudinal portions thereof which are far removed from its end anchorages.

Conventional load testing of post-tension slabs may also be attempted to evaluate the condition of the prestressing elements, but such load testing does not necessarily provide reliable information about whether or where the prestressing elements are corroded, nor any indication of whether any on-going corrosion activity can be expected to continue to reduce the slab load bearing capacity. Moreover, conventional load testing is both costly and time consuming.

Finally, methods employing either ultrasonic or acoustic emission techniques or electrical conductivity techniques have been proposed for determining the structural soundness of prestressing elements, but some have found that such methods are not necessarily workable in that a reliable correlation between the test results produced by these methods and the actual corrosion condition of the prestressing elements is difficult to ascertain.

None of the prior art methods discussed above for the on-site evaluation of unbonded prestressing elements is suitable nor easily adaptable for the treatment and corrosion protection of prestressing elements once they have been evaluated. Thus, the known methods of evaluation cannot be resorted to for restoring a prestressing element to an acceptably dry condition nor for protecting the restored element from further corrosion.

It is therefore one object of the present invention to provide a relatively reliable and cost-effective method for the non-destructive condition evaluation of unbonded prestressing elements in post-tension concrete structures, so as to enable a determination of the corrosion condition of such prestressing elements and their susceptibility to further corrosion.

It is another object of the present invention to provide a method and apparatus for the evaluation of prestressing elements by sampling and assessment of the gaseous environment contained within the conduit means of the prestressing element.

It is a further object of the present invention to provide a said method and apparatus which will also serve in the treatment of the gaseous environment within the conduit means of prestressing elements by removing moisture, bulk water and other impurities conducive to corrosion from within the conduit means.

It is yet another object of the present invention to provide the said method and apparatus which will also enable the detection of leaks and probable points or areas of moisture and corrosive agent penetration in the concrete cover and anchorage ends.

It is yet another object of the present invention to provide a said method and apparatus which facilitate long-term maintenance and protection of the prestressing element environment by continuous or cyclic pressurization and replenishment of the gaseous environment within the conduit means of the prestressing element with a dry non-corrosive gas.

It is also an object of the present invention generally to attempt to overcome the problems and deficiencies occasioned by the prior art methods of evaluating, treating and protecting unbonded prestressing elements in post-tension concrete structures.

These and other objects are sought to be attained by way of the present invention, as more fully described and illustrated herebelow.

SUMMARY OF THE INVENTION

According to one broad aspect of the present invention, there is provided an on-site method for the corrosion condition evaluation of unbonded prestressing elements in post-tension concrete structures in service, said elements each being disposed within a respective conduit means, said conduit means containing a gaseous environment to which said elements are subjected, the method comprising the steps of:

(a) locating a said post-tension prestressing element within said concrete structure;

(b) providing at least two openings in said concrete structure at respective positions along the longitudinal length of said prestressing element and between terminal ends thereof, one of said openings being an inlet port and the other of said openings being an outlet port, the said ports each permitting communication with said gaseous environment in said conduit means;

(c) accessing said gaseous environment through said outlet port by extracting a sample of gas from said environment through said outlet port; and (d) measuring said gaseous environment sample accessed through said outlet port to determine its humidity and thereby evaluate the corrosion condition of said prestressing element between said inlet port and said outlet port.

With reference to preferred embodiments of the present invention according to the first broad aspect thereof, the method further includes the steps of providing a source of dry non-corrosive gas in communication with the inlet port and subjecting the gaseous environment within the conduit means to the source of dry gas at a pressure and for a time sufficient to expel a sample of the gaseous environment through the outlet port for measuring the sample for humidity. Successive samples of the gaseous environment are expelled through the outlet port at predetermined time intervals, each such sample being measured to determine its humidity. This preferred method therefore enables the sampling and measurement of representative samples of the gaseous environment within the conduit means along the whole of the length of the element between the inlet port and the outlet port.

According to a second broad aspect of the present invention, there is provided an apparatus for the on-site corrosion condition evaluation of unbonded prestressing elements in post-tension concrete structures in service, said elements each being disposed within a respective conduit means, said conduit means containing a gaseous environment to which said elements are subjected, the apparatus comprising:

(a) a supply means for supplying a dry non-corrosive gas;

(b) at least one inlet port and at least one outlet port, each port being provided in said concrete structure at respective positions along the longitudinal length of a said prestressing element and between terminal ends thereof, said ports each permitting communication with said gaseous environment in said conduit means;

(c) means for sampling and measurement of said gaseous environment to determine the humidity thereof;

(d) a regulator means to regulate pressure and flow rate of said dry gas; and whereby said gaseous environment within the conduit means is subjected to a flow of said dry gas from said supply means and through said inlet port, said regulator means being adjusted to provide said flow of dry gas at a pressure and for a time sufficient to extract a sample of said gaseous environment through said outlet port to said means for sampling and measurement to determine the humidity of said sample and thereby evaluate the corrosion condition of said prestressing element between said inlet port and said outlet port.

According to a third broad aspect of the present invention, there is provided an apparatus for the on-site corrosion protection of unbonded prestressing elements in a post-tension concrete structure in service, said elements each being disposed within a respective conduit means, said conduit means each containing a gaseous environment to which said elements are subjected, the apparatus comprising:

(a) inlet ports provided in said concrete structure, said inlet ports being located at respective positions along the longitudinal lengths of each of said prestressing elements and between terminal ends thereof, said inlet ports respectively permitting communication with said gaseous environments in said conduit means;

(b) a supply means for supplying a site-manufactured dry non-corrosive gas through said inlet ports and to said conduit means;

(c) an automatic controllable valve means for said supply means; and (d) a programmable control means, said control means constituting means for actuating said controllable valve means to thereby cyclically pressurize said conduit means with said dry gas provided through said inlet ports for a selected duration of time and according to a selected time schedule.

According to a fourth broad aspect of the present invention, there is provided an on-site method for the corrosion protection of unbonded prestressing elements in a post-tension concrete structure in service, said elements each being disposed within a respective conduit means, said conduit means each containing a gaseous environment to which said elements are subjected, the method comprising the steps of:

(a) locating a plurality of said post-tension prestressing elements within said concrete structure;

(b) providing at least one inlet port in said concrete structure for each of said prestressing elements, said inlet ports being located at respective positions along the longitudinal lengths of said prestressing elements and between terminal ends thereof, the said inlet ports respectively permitting communication with said gaseous environments in said conduit means;

(c) providing a source of dry non-corrosive gas in communication with said inlet ports;

(d) subjecting said gaseous environments in said conduit means to said source of dry gas so as to cyclically pressurize each of said conduit means according to a selected time schedule with said dry gas at a selected flow rate thereof and for a selected time duration of pressurization;

(e) periodically accessing the gaseous environments of a preselected number of said prestressing elements for measurement of said gaseous environments to determine the humidity thereof;

(f) comparing said measured humidity with a predetermined maximum humidity value; and (g) adjusting said flow rate, said time duration and said time schedule of cyclic pressurization so as to maintain said predetermined maximum humidity value in the gaseous environments of each of said preselected number of prestressing elements between cycles of pressurization.

BRIEF DESCRIPTION OF DRAWINGS

For purposes of illustration, but not of limitation, preferred embodiments of the present invention are described hereinbelow with reference to the following drawings in which.

DETAILED DESCRIPTION OF PREFERRED EMBODIMENTS

Figure 1:
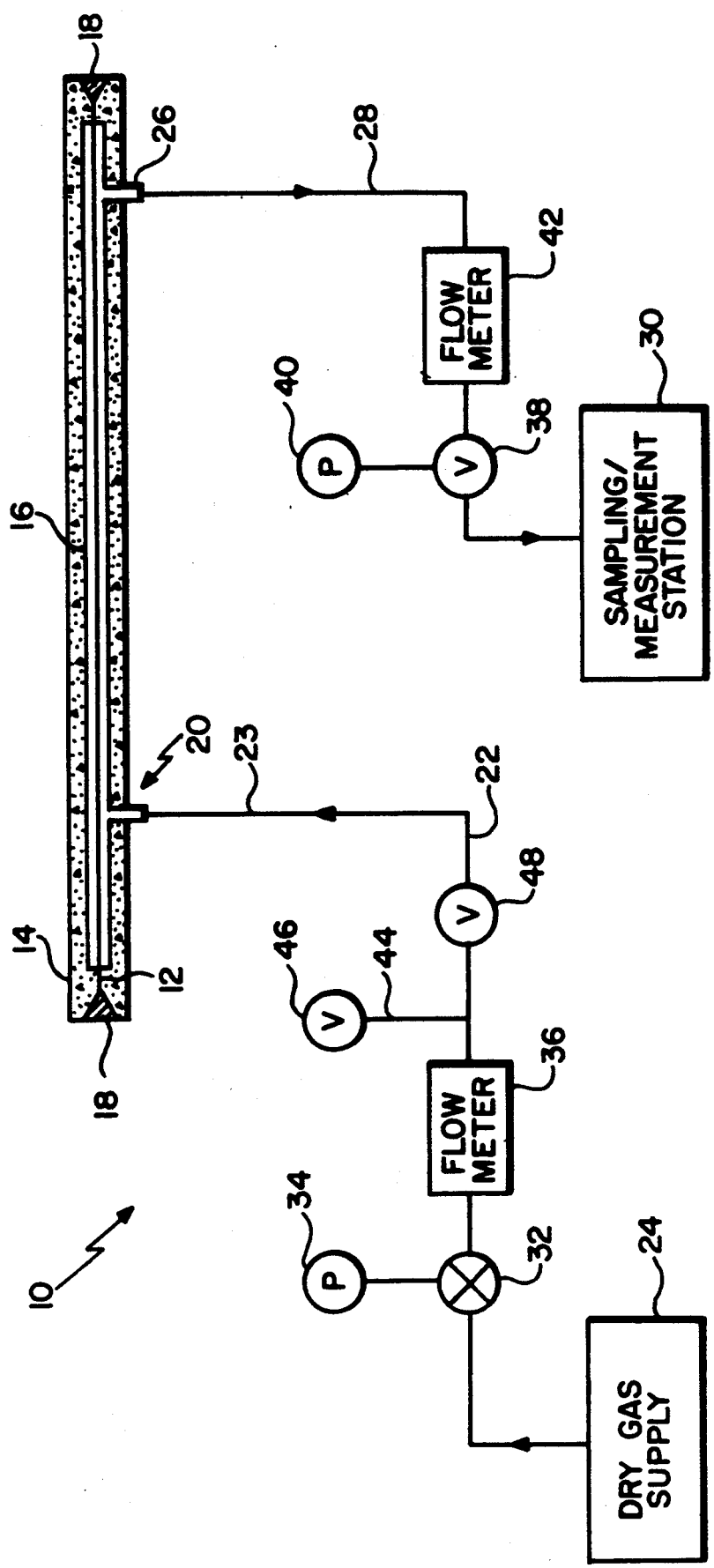
FIG. 1 is a schematic representation of a dry gas system for the evaluation and protection of an unbonded prestressing cable in a concrete slab according to the present invention.

The dry gas evaluation and protection system 10 is used for the on-site non-destructive condition evaluation, treatment and protection of an unbonded prestressing element such as a prestressing cable 12 in service in a concrete member such as a slab 14. The prestressing cable 12 is disposed in a conduit means, for instance a plastic cable sheath 16. When in service, the prestressing cable 12 will be in a tensioned condition, the cable being secured at each of its terminal ends to the extremities of the concrete slab 14 by means of cable end anchorages shown in schematic form as at 18.

It is generally known that a steel cable subjected to a gaseous environment having a relative humidity of more than approximately 60% will be vulnerable to corrosion in the presence of oxygen. It is also generally known that where the relative humidity of such a gaseous environment is maintained to below approximately 45% the susceptibility to corrosion is reduced.

As set out in greater detail below, the evaluation and protection system 10 may be used to assess the corrosion condition of a given prestressing cable 12 in a concrete slab 14 by extracting a volume of gas from the gaseous environment contained in the cable sheath 16 and measuring the extracted volume of gas at a sampling and measurement station 30 to determine its humidity. The extraction of gas from within the cable sheath 16 is preferably achieved by subjecting the gaseous environment within the cable sheath 16 to a source of dry non-corrosive gas from a dry gas supply 24 by way of a supply line 22, branch line 23 and inlet ports 20. The gas is supplied through the inlet ports 20 to the inside of the cable sheath 16 at a pressure and for a time sufficient to expel a sample of the gaseous environment within the cable sheath 16 through an outlet port 26 and into a gas discharge line 28 for sampling and measurement at the station 30.

Preferably, the determined humidity of the extracted sample of gas is the specific humidity thereof, which may in turn be derived from measurements of both the temperature and relative humidity of the gas. As explained below, those skilled in this art will readily be able to derive, from the specific humidity, the relative humidity of the gas samples at various temperatures. In this way, the corrosion condition of a prestressing element may be evaluated by assessing whether the relative humidity of the conduit gas environment of the element exceeds the 45% to 60% levels mentioned above over the typical range of temperatures to which the concrete structure is subjected.

Where it is desired to employ the evaluation and protection system 10 in order to treat a prestressing cable 12 by drying it, one has only to purge the cable sheath 16 with dry gas from said dry gas supply 24 so as to substantially replace the original gaseous environment within the cable sheath 16 and so as to permit the dry gas to entrain any localized moisture or condensation within the sheath 16. The accomplished degree of drying of the gaseous environment within the cable sheath 16 can be verified and monitored by appropriate sampling and measurement of expelled gas through the gas discharge line 28.

Where it is sought to achieve long term corrosion protection of the prestressing cable by maintaining a desired degree of dryness of the gaseous environment within the cable sheath 16, a manual shut-off valve 48 in the supply line 22 may be replaced with a controllable valve means such as a solenoid valve as further discussed below. In this manner, a given post-tension structure may be protected from further corrosion by continuous or periodic purging of any desired number of cable sheaths 16 of the structure.

In order to install the dry gas evaluation and treatment system for the prestressing cable 12, it is first necessary to locate such a cable within the slab 14. This may be accomplished by means well-known to those skilled in this art, such as by using a cover meter or pachometer which assists in determining the depth and location of metal elements embedded in concrete. Other such means for locating the prestressing cable within the slab will be readily apparent to those skilled in the present art.

Once a selected prestressing cable 12 has been located, one or more gas inlet ports 20 are provided in the concrete slab 14 along the longitudinal length of the prestressing cable 12 at desired locations between the terminal ends of the cable. As will be explained in greater detail herebelow, the gas inlet ports 20 are provided to permit communication with the gaseous environment contained within the cable sheath 16.

The gas inlet ports 20 are connected to a gas branch line 23 which connects to the gas supply line 22 which in turn is connected to a dry gas supply 24. By way of example, the dry gas supply line may be provided in the form of rigid 1⅜ in. (or 40 mm) diameter P.V.C. or A.B.S. plastic tubing. The gas branch line 23 may be in the form of flexible ¼ in. (or 6 mm) diameter plastic tubing. The dry gas supply 24 provides a source of dry, non-corrosive gas to the said gas inlet ports 20. As explained in greater detail below, the dry gas may be nitrogen gas supplied from pressurized canisters or ambient air which has been dried on-site to sufficiently reduce its moisture content to an acceptable level. Those skilled in this art will appreciate that any other non-corrosive dry gas may be employed for the dry gas supply 24.

One or more gas outlet ports 26 are also provided in the concrete slab 14 at desired positions along the longitudinal length of the prestressing cable 12 between its terminal ends. As is the case with the gas inlet ports 20, the gas outlet ports 26 permit communication with the gaseous environment contained in the cable sheath 16. The structure and locations of the gas outlet ports 26 are described in greater detail below.

A gas discharge line 28 is connected to one of the outlet ports 26, thereby permitting the sampling and measurement of the gaseous environment within the cable sheath 16 at a sampling and measurement station 30, as discussed below. The gas discharge line 28 may be of similar Construction to the gas branch line 23 described above.

The gas supply line 22 may be provided with gas flow control means to respectively control the flow rate and pressure of dry gas and expelled gas respectively to and from the cable sheath 16. For instance, in the case of the gas supply line 22, a regulator valve 32, a pressure gauge 34 and a flow meter 36 may be provided in the gas supply line 22 at positions downstream from the dry gas supply 24 for this purpose. In the case of the gas discharge line 28, a similar set consisting of valve 38, pressure gauge 40 and flow meter 42 may be disposed in the gas discharge line 28, for instance at a location upstream from the sampling and measurement station 30. The flow meter 42 may incorporate a needle valve for adjusting the rate of outflow of gas in the discharge line 28. Alternatively, the valve 38 may be used to adjust the flow rate.

The gas supply line 22 may also advantageously be provided with a supply sampling line 44 whose terminal end downstream from the supply line 22 is provided with a manual shut-off valve 46. When it is desired to sample the dry gas in the supply line 22, for instance in order to monitor or verify the moisture content of the gas, one has only to open the valve 46 in order to direct the flow of dry gas through the supply sampling line 44. A second shut-off valve 48 may be provided in the supply line 22 as a convenient means of preventing the supply of dry gas to the conduit means whenever desired.

Figure 2:
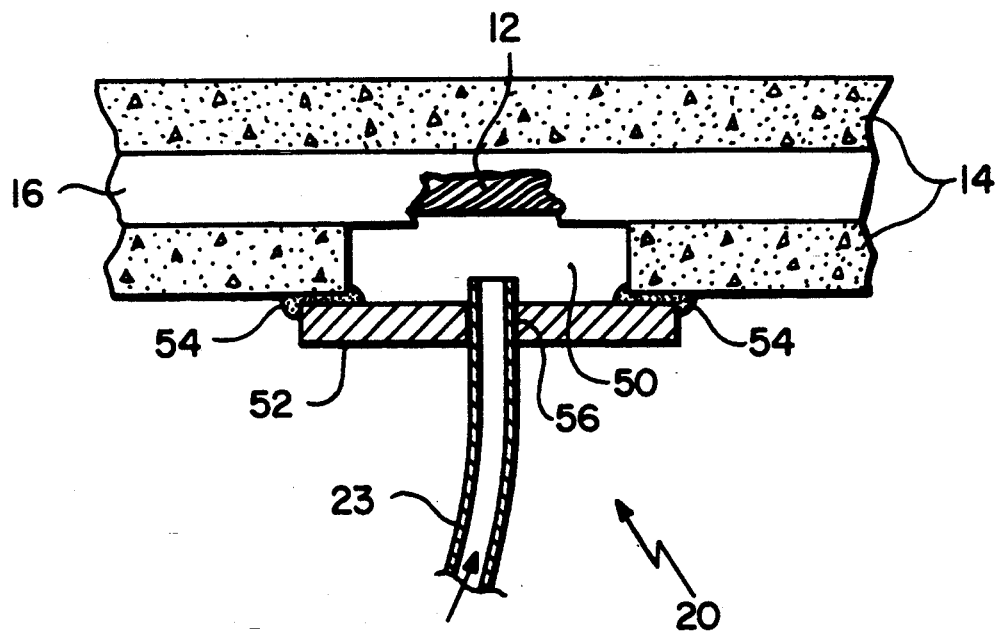
FIG. 2 is a detailed cross-sectional longitudinal view in elevation of an inlet port for the dry gas system of FIG. 1.

FIG. 2 shows a preferred configuration for the dry gas inlet port 20. A cavity or inspection bay 50 is excavated into the underside of the slab 14 to expose a prestressing cable 12 located within its cable sheath 16. By way of example, the inspection bay 50 may be in the form of a squared opening with sides being of the order of 5 in. (or 12.5 cm) in length. The cable sheath 16 can then be cut open to expose a desired length of prestressing cable 12, for instance 4 in. (or 10 cm). Exposing the cable 12 in this manner permits communication with the gaseous environment contained therewithin. A removable cover means such as a flat metal plate 52 or other like covering is provided to completely cover the perimeter of inspection bay 50, and may be secured to the concrete slab by screw fasteners (not shown) or the like. A substantially air-tight seal may be obtained by applying a suitable caulking 54 around the outside perimeter of the top surface of the plate 52. The metal plate 52 is provided with a bore 56 therein for admitting the dry gas branch line 23. In this manner, the gaseous environment within the plastic cable sheath 16 may be subjected to a flow of dry gas from the dry gas supply 24.

Figure 3:
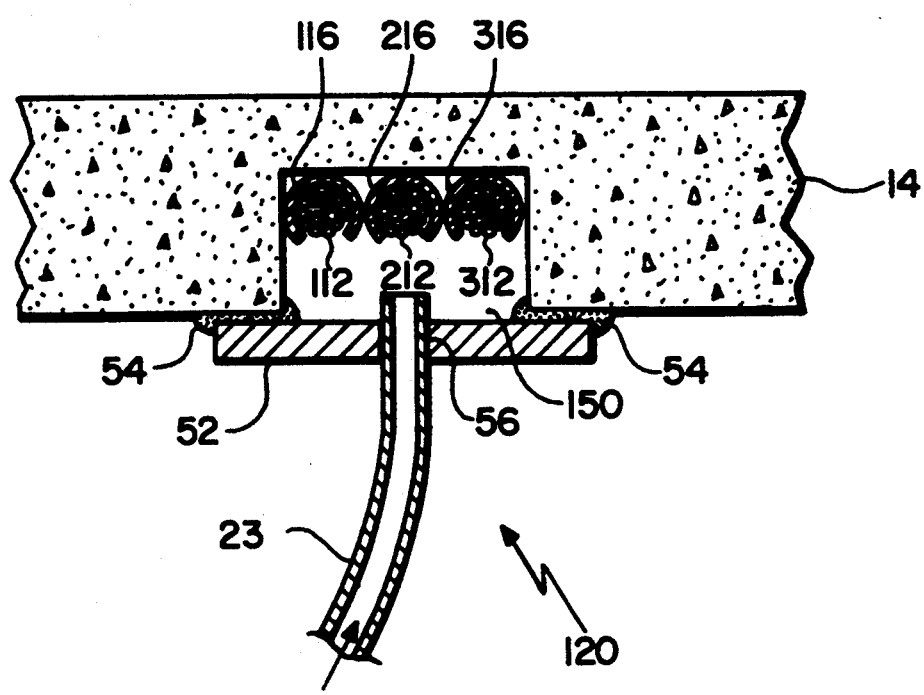
FIG. 3 is a detailed cross-sectional axial view in elevation of an alternative inlet port for the dry gas system of FIG. 1, showing three prestressing cables in a side-by-side arrangement.

An alternatively configured gas inlet port 120 is illustrated in FIG. 3, wherein a set of three prestressing cables 112,212,312 are disposed side-by-side within a single inspection bay 150 within their respective cable sheaths 116,216,316. I have found that it is possible to supply the gaseous environments contained in each of a plurality of cable sheaths such as three cable sheaths 116,216,316 by means of a single inspection bay 150 and supply line 22.

Figure 4:
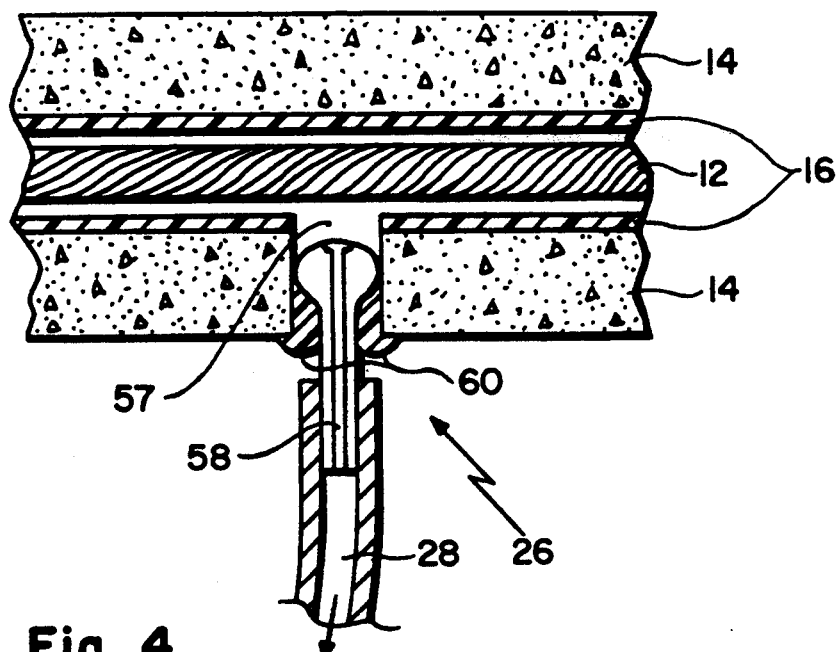
FIG. 4 is a detailed cross-sectional longitudinal view in elevation of an outlet port for the dry gas system shown in FIG. 1.

Details of an outlet port suitable for the present invention are illustrated by FIG. 4. The gas outlet port comprises an opening or bore 57 in the concrete slab 14 extending through the cable sheath 16 and permitting communication with the gaseous environment within the sheath. Into the opening 57 is inserted a valve means such as a valve stem 58 with a cap (not shown), such a valve stem being in common use in automobile pneumatic tires. A substantially air-tight seal between the valve means 58 and the opening 57 may be achieved by means of an epoxy sealant 60 or the like.

Although a single gas inlet port may be used to supply dry gas to a plurality of cables as shown in FIG. 3, a separate gas outlet port 26 should be employed where possible for each prestressing cable, so as to enable sampling and measurement of the gas environment contained in one particular cable sheath 16, and therefore one particular cable 12, at a time. Even in instances where prestressing cables are disposed in a side-by-side configuration for most of their lengths within a given span of concrete slab, it is customary for such grouped cables to fan out one from the other in a spaced apart configuration at the ends of the slab so as to allow sufficient spacing for the cables at their ends for anchoring purposes. As such, it may be possible to isolate single cables for locating a dedicated outlet port for use in conjunction with a cable, even where prestressing cables are disposed in a given concrete structure in a grouped configuration. At times, however, it may not be possible to avoid the puncture of more than a single cable sheath 16 when providing outlet ports 26 in the concrete slab 14. As well, air spaces may exist in a given slab below or above grouped cables, such that crossflow of the gaseous environment within the sheaths of such cables will result. In all such instances, sampling and measurement through an outlet port 26 will not be restricted to the isolated gaseous environment of its respective cable sheath, but will reflect the environments of two or more grouped cables, as the case may be.

Those skilled in this art will appreciate that where prestressing cables are disposed in a concrete structure in a spaced apart configuration and not in a grouped configuration as discussed previously, gas inlet ports may, if desired, be in the form of bores extending through the concrete rather than in the form of inspection bays 50 or 150. It may also be possible in the case of grouped cables to locate and isolate each cable member individually and provide it with a dedicated gas inlet port in the form of a bore. However, the advantage of an inspection bay is that of enabling a visual inspection of selected prestressing cables for signs of corrosion and for the presence of water or of grease or other corrosion inhibiting agents. As well, it is possible to roughly test the cables for tightness, for instance by manually prying at a cable through the inspection bay with the aid of a crowbar or the like. It will also be appreciated that by securing the plates 52 with screw fasteners and by sealing the inspection bays 50 or 150 with caulking, the plates 52 are therefore removable for intermittent visual and physical inspection of the prestressing cables which are provided with such inspection bays.

It will also be appreciated by those conversant in the art that the outlet ports 26 may serve as grease injection ports if it is desired to protect prestressing cables with a grease once they have been treated by drying according to the present invention. Where the grease cover was inadequate initially or the original grease or other corrosion inhibiting cover has become ineffective over time, it will therefore be possible to substitute a high quality protective product by injection through the outlet ports 26.

Figure 5:
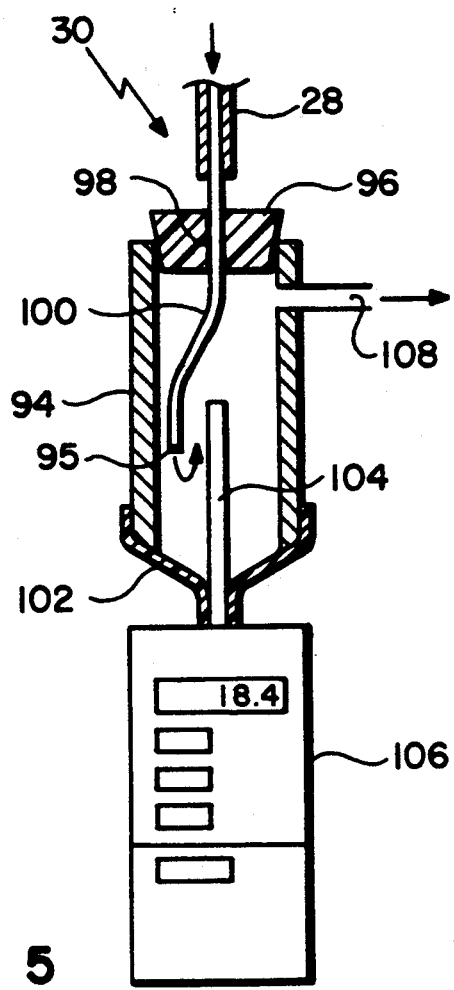
FIG. 5 is a detailed partial cross-sectional view of a sampling and measurement station for the dry gas system of FIG. 1.

Turning now to FIG. 5, an exemplary sampling and measurement station 30 for the dry gas evaluation and protection system 10 comprises a sampling chamber 94, which may be in the form of a hollow cylindrical tube open at each of its ends. The upstream end of the chamber 94 is sealed with a rubber stopper 96 or the like, the stopper having a bore 98 therein to admit a chamber inlet tube 100. The downstream end of chamber 94 is sealed with a rubber bladder 102 or other suitable means, with a measurement probe 104 of a relative humidity/temperature meter 106 passing therethrough and into the chamber.

The gas discharge line 28 from outlet port 26 is connected to the outside end of chamber inlet tube 100. The other open end of the inlet tube 100 which is within chamber 94 is disposed adjacent the downstream end of the chamber, as at 95. An open exhaust port 108 is provide adjacent the upstream end of the chamber, and the terminal end of the probe 104 is located between open end 95 of the inlet tube 94 and the exhaust port 108. This configuration enables the gas entering the chamber at the downstream end thereof to effectively flush out existing gas in the chamber upwardly and out through the exhaust port 108, to thereby provide a representative sample of the current discharge gas relatively free from contamination by earlier gas samples.

Those skilled in this art will appreciate that the use of a discharge line 28 is optional, since it is possible to directly connect the chamber inlet tube 100 to the outlet port 26. Where it is used, however, it will be appreciated that the discharge line 28 should be made as short as possible so as to reduce the volume of existing gas therewithin which must be displaced or purged prior to taking measurements of the gaseous environment within the gas sheath 16.

Figure 6:
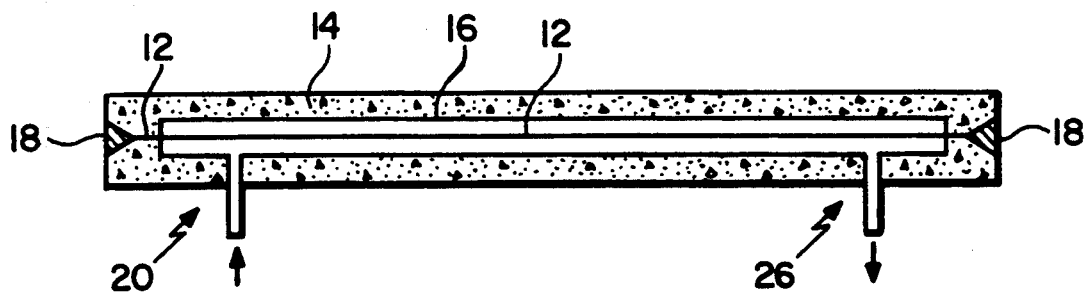
FIGS. 6, 7 and 8 are schematic representations of an unbonded prestressing cable in service in a concrete slab, showing various configurations for the supply and egress of gas to and from the cable.
Figure 7:
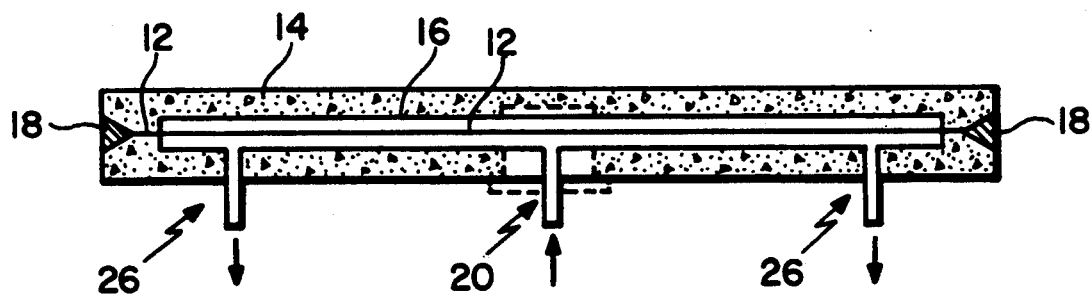
Figure 8:
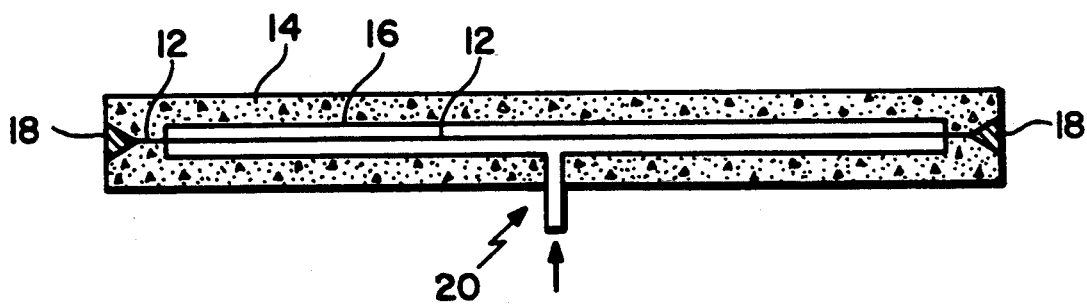

With regard to FIGS. 6, 7 and 8, various configurations of gas inlet and gas outlet ports may be employed with the evaluation and protection system 10 according to the present invention. Thus, in FIG. 6, a single gas inlet port 20 is provided adjacent one of the terminal ends of prestressing cable 12 while a single outlet port 26 is provided adjacent the other terminal end of the cable. Dry gas provided from the dry gas supply 24 through the supply line 22 enters the inlet port 20 at one extremity of the cable 12 and purges the gaseous environment within the cable sheath 16 by displacing it towards the other extremity of the cable 12 and through the outlet port 26. Those skilled in the art will appreciate that some portion of the gaseous environment within the cable sheath may be purged by exiting through leaks in the concrete slab 14, for instance through cracks therein. This phenomenon can be used to assess potential points of moisture penetration in the concrete cover, by localizing escaping gas during pressurization of the cable sheaths 16 with dry gas. Such points of moisture ingress may then be sealed to minimize future moisture penetration. The configuration illustrated by FIG. 6 may be used both in the evaluation of the corrosion condition of a given cable 12 and in its treatment or protection by repeated purging with dry gas.

In FIG. 7, a single inlet port 20 is provided, centrally located along the longitudinal length of the cable 12 between the cable end anchorages 18. Two gas outlet ports 26 are provided for the cable sheath 16, one adjacent each terminal end of prestressing cable 12. This configuration is advantageous in evaluating or treating a prestressing cable 12 which has localized areas of water pooling or condensation. This is because dry gas fed from the center of the prestressing cable 12 will flow outwardly through the cable sheath displacing the existing gaseous environment therewithin towards each end of the slab. In this manner, any localized moisture at one end or the other of the prestressing element is not moved through the whole length of the slab as is the case with the configuration shown by FIG. 6. Thus, FIG. 7 illustrates the preferred configuration for the evaluation and protection of unbonded post-tension prestressing elements.

In the configuration shown by FIG. 8, a single gas inlet port 20 is provided. Such a configuration is more suitable for treatment and protection of prestressing cables 12 than for their evaluation, since dry gas supplied through the inlet port is only permitted to exit the cable sheath through gas leaks in the concrete slab 14.

The configurations of FIGS. 6 and 7 allow for measurement of the gaseous environment within the cable sheath to be made by extracting a volume of gas therefrom through the outlet ports 26, such that representative samples of the gaseous environment at different locations along the cable sheath will result by intermittent measurement of the discharge gas during pressurization of the cable sheath. Nonetheless, those skilled in the art will appreciate that measurement of the gaseous environment associated with a cable sheath 16 in the configuration of FIGS. 6 and 7 may be achieved by accessing the said environment through the said outlet ports or through one or more additional bores (not shown) in the concrete slab, by means of which a respective humidity measurement means such as an embedded measurement probe or sensor of a gas humidity measurement system will be introduced. Since such probes would access the gaseous environment of the cable sheath at fixed locations therealong, care must be taken with such a method of measurement so as to ensure that the probes only be utilized where good gas flow has already been established in the cable sheath.

If desired, the configuration illustrated by FIG. 8 may be used for the protection of a number of prestressing cables in a post-tension array in conjunction with the configuration of FIG. 7 for selected cables of the array. These selected cables would constitute control cables and would permit monitoring of the gaseous environment within the control cables as a means of assessing the progress and effectiveness of drying. This is addressed in greater detail below. Those conversant in this art will understand that other inlet/outlet port configurations can be used with the present invention.

As briefly discussed previously, the potential for corrosion of steel in the atmosphere increases rapidly as the relative humidity increases above approximately 60%, and this susceptibility to corrosion reaches a peak at relative humidity levels in the approximate range of 85% to 95%. Below a relative humidity of approximately 45%, on the other hand, the potential for corrosion of steel is generally believed to be low. Although temperature is also a factor which influences the potential rate of corrosion, this factor by itself is believed to influence corrosion potential to a much lesser degree than relative humidity. However, as explained below, temperature has an important indirect effect on corrosion in a sealed environment since temperature will affect the relative humidity of such environments.

The gaseous environments of the cable sheaths in a prestressing array may be considered to define an enclosed environment for each cable or cable grouping, at least for short periods of time of the order of several days. As such, it is generally not sufficient to sample and measure the relative humidity of the gaseous environment of a cable sheath in order to properly assess the corrosion condition of the prestressing cable therewithin or its susceptibility to further corrosion, when such a cable is subject to wide and cyclic variations of temperature. This is because the relative humidity of an air mass is a parameter which fluctuates with temperature. For example, a single sample of the gaseous environment of a given cable sheath may reveal a measured relative humidity of 45% at 30° C., and at first impression such a relative humidity level may not be thought of as being very conducive to corrosion. However, a drop in temperature (for instance as may occur overnight) to only 17° C. would result in the very same cable environment having a relative humidity of 100%, which is very conducive to corrosion. A further decrease in temperature would cause condensation of water within the same cable sheath, and if the condensated water has not re-evaporated by the time a sample of the gaseous environment is being measured for its relative humidity, the measured readings could incorrectly suggest the potential for corrosion to be low, since the gaseous environment within the cable would temporarily have a reduced moisture content due to the condensation.

Those skilled in the present art will understand the importance when assessing the corrosion condition of cables that are subject to wide temperature variations to begin with a determination of the specific humidity or absolute humidity of the cable sheath gaseous environments, and not to rely simply on measurements of relative humidity. This is because the specific humidity and absolute humidity of a gas in a relatively sealed system such as the cable sheath remains constant unless condensation occurs, whereas relative humidity will vary with temperature. By "specific humidity", what is intended herein is to designate a ratio of the mass of water vapour in the gaseous environment of the cable sheath to the mass of dry air contained therewithin, typically represented as Kg of $H_2O$ per Kg of dry air. By "absolute humidity", what is intended herein is to designate a ratio of the mass of water vapour present to the total volume occupied by the mixture. For a gaseous environment such as that contained within a cable sheath, each of these measures of humidity can be expected to remain constant with variations of temperature. Those skilled in the art will appreciate that the specific or absolute humidity within a cable sheath may also be represented by an equivalent temperature invariant measure of humidity, such as dew point. Thus, what is to be understood herein by "specific humidity" is any appropriate measure of humidity or moisture content which is for practical purposes temperature invariant in the context of the gaseous environments contained within the conduits of unbonded prestressing elements.

Those skilled in this art will readily be able to determine specific humidity or dew point by measurements of both temperature and relative humidity, for instance by known psychometric principles. Once the specific humidity or dew point for a given cable sheath environment is known, those skilled in the art will easily be able to derive the respective relative humidity levels of the gaseous environment for the different temperatures at which the concrete structure is likely to be subjected. As well, the moisture content measurement of the cable environment can be used in conjunction with the most recent low daily temperatures preceding a measurement in order to determine the likelihood of prior condensation in the cable sheath. If prior condensation is suspected, measurements of the relative humidity and temperature of gaseous environment may be repeated over the course of a few days in order to obtain more reliable readings of the actual moisture content associated with the cable sheath gaseous environment.

Once the cables of a given prestressing array have been located as described above and the desired inlet and outlet port configurations have been provided for a selected number of cables in the array, the evaluation and protection system 10 may be operated to sample and measure the gaseous environment within the cable sheaths of the selected cables so as to evaluate their corrosion condition. The cable sheath environments to be evaluated are first pressurized with dry gas from the dry gas supply 24. To do so, the shut-off valve 48 of supply line 22 is opened and the regulator valve 32 is used to adjust the downstream pressure and flow rate of the dry gas. As soon as possible after pressurization, a gas discharge line 28 is connected to an outlet port 26 of the cable, and sampling and measurement of the discharged gas is then performed at station 30 to obtain its relative humidity and temperature.

It is important to sample and measure the discharge gas soon after pressurization so as to minimize the effect of gas loss from the cable sheath through any cracks in the concrete cover. Moreover, those skilled in the present art will understand that several successive readings of temperature and relative humidity should be taken for a given cable sheath, so that measurements are not made of existing gas within the sampling chamber 94 or of the existing gas within the discharge line 28, but rather of the actual gaseous environment within the cable sheath 16. The flow rate in the gas discharge line 28 should be adjusted so that sampling and measurement can be performed under similar gas flow conditions at the discharge line 28 for each cable being evaluated.

In the preferred method of condition evaluation of prestressing elements in a post-tension structure according to the present invention, successive samples of the gaseous environment within the cable sheath are expelled through the outlet ports 26 at predetermined time intervals and at a constant flow rate of dry non-corrosive gas. This enables the sampling and measurement station 30 to receive representative samples of the gaseous environment within the prestressing element sheath 16 along the whole of the length of the element 12 between the inlet port 20 and outlet port 26. This therefore allows for the sampling and measurement of any pockets or segments of high moisture content along the length of the prestressing element to permit recordal of the highest moisture content of the gaseous environment it is subjected to.

As discussed above, the possible existence of water condensate in a sheath may mask the potential for corrosion if not taken into account. Where resources permit, those skilled in this art will appreciate that repeated sampling and measurement on different consecutive days of the gaseous environment of the cable sheaths may provide a more accurate and detailed assessment of the actual moisture content associated with the sheaths if recent condensation is suspected. In these cases, the cable sheaths 16 are left unpressurized between the successive readings to prevent purging of the gaseous environment within the sheaths, and pressurization is done immediately prior to each daily reading. In such cases, the skilled person will also understand that sampling and measurement of discharge gas should preferably be undertaken at warmer temperatures, when rates of re-evaporation of water condensate will be enhanced.

At times, blockages within the cable sheaths 16 caused by grease or entrapped contaminants may prevent the unrestricted flow of dry gas through a sheath. When this is experienced, increasing the pressure of dry gas to the gas supply line 22 may cause clearing of the sheath. Once so cleared, the pressure of dry gas may be reduced to obtain a desired discharge gas flow rate in the discharge line 28. Where the cable sheath 16 cannot be cleared by the above procedure, the particular cable or section of cable will not be capable of evaluation and protection by way of the present invention.

The skilled person conversant with the field of the present invention will understand that other means of accessing the gaseous environment within a cable sheath may be adaptable for use with the present invention. For instance, applying suction to the discharge line 28 may be an alternative to pressurization applied at the supply line 22. The skilled person will take the necessary precautions to ensure that sampling and measurement of the cable sheath gaseous environment when using suction at the discharge line are not unduly influenced by ambient air being drawn into the cable sheath through cracks in the concrete cover. Another alternative means of accessing the cable environment and its limitations are discussed above and consists of inserting a fixed measurement probe through the concrete slab and into the cable sheath.

Those skilled in the art will also appreciate that additional parameters other than relative humidity and temperature may be measured in the gaseous environment of the cable sheath and utilized to assess the cable condition. For instance, it may be found by some to be useful to analyze the said environment for the presence or concentration of various constituent component gases such as oxygen, carbon dioxide or hydrogen, to name a few.

The method and apparatus according to the present invention are also suitable for the treatment and protection of unbonded post-tension prestressing elements. The treatment of prestressing elements such as cables consists of the continuous or intermittent purging of the cable sheaths using the dry gas system 10 in conjunction with regular sampling and measurement of the discharge gas as previously explained. By periodic sampling and measurement of the discharged gas through outlet ports 26 for its moisture content, it is possible to assess the progress and permanency of cable drying by gas purging. For instance, where a cable sheath gas environment shows continued high levels of moisture in the discharge gas after repeated dry gas purges, this will generally indicate a cable which has relatively open communication with the outside atmosphere. In such cables, the points of entry for moisture and contaminants must be identified and sealed in order for dry gas purging to effectively dry the cable.

Once a cable has been dried, long-term protection may involve re-injection of high quality grease or some other corrosion inhibitor through the discharge gas outlet ports, as previously explained. However, where a cable has exhibited persistently moist discharge gas during intermittent or continuous dry gas purging, such a cable should be subjected to a full length inspection by traditional methods, since it will be of little consequence to re-inject a fully failed and corroded cable with grease.

The present invention may also be used as an alternative to re-injection of the cables with a corrosion inhibitor. The cables of a post-tension structure may be subjected to continuous or cyclic pressurization on a long-term basis in order to effectively minimize corrosion and on-going deterioration of the cables at a relatively low cost. The moisture content of the cable sheath gaseous environments may be monitored during pressurization, and the pressure, flow rate, time duration and time schedule or frequency of pressurization adjusted accordingly to maintain a maximum permissible moisture content in the sheaths.

Figure 9:
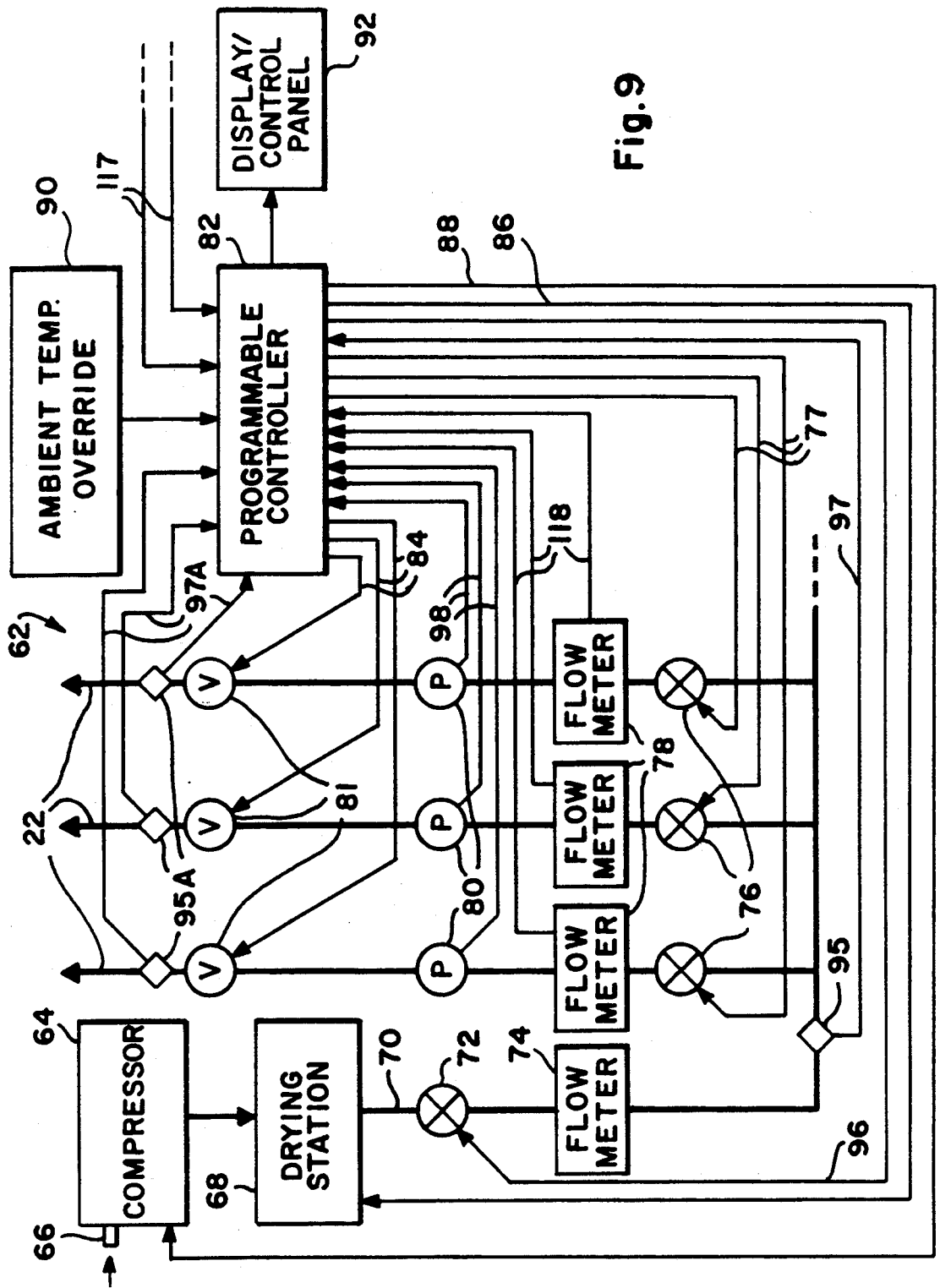
FIG. 9 is a detailed schematic representation of a site-manufactured dry gas supply having programmable control means for the dry gas system as shown in FIG. 1.

A programmable dry gas supply station as illustrated by FIG. 9 may advantageously be employed with the evaluation and protection system 10, especially where the system 10 is to be used for a long-term treatment and protection of prestressing elements in a concrete structure. The programmable gas supply station includes a compressor 64 with an ambient air intake 66. The ambient air is pressurized by the compressor 64 and is then supplied to a drying station 68 where the pressurized ambient air is dried to a humidity level with a low dew point, for instance $-40°$ C. By way of example, the ambient air may be dried in this manner by means of a rotary screw-type air compressor and a heatless regenerating desiccant dryer. One suitable compressor is distributed by Sullair Corporation of Michigan City, Ind., U.S.A. under model designation 6E 10.0H. One suitable heatless dryer is manufactured by Wilkerson Corporation of Englewood, Colo., U.S.A. and is designated as model DE4. Other suitable apparatus will be known to those conversant in this field of art.

Site manufactured dry gas such as dried ambient air may be used with the present invention since it can be more economically produced in large volumes when compared with bottled dry gas. Other site manufactured dry gases may also be suitable for use with the present invention. Some of these other dry gases would have the additional benefit over dried air of not only removing moisture from within the cable sheaths but also of purging oxygen therefrom.

From the drying station 68, the dried ambient air enters a main supply line 70, which may be provided with a regulator valve 72 and flow meter or sensor 74 to obtain a desired pressure and flow rate of dried ambient air in the main supply line 70. A plurality of gas supply lines 22 may then be disposed along the main supply line 70 in order to supply dried ambient air to a desired number of prestressing cables 12 of a concrete structure. Each supply line 22 may be provided with regulator valves 76, flow meters or sensors 78 and pressure gauges or sensors 80 for adjustment and control of dried gas flow in each of the individual supply lines 22.

Each gas supply line 22 is further provided with an automatic controllable valve means such as a solenoid valve 81. The solenoid valves 81 may be controlled by means of a programmable controller 82 which can be programmed to operate the valves by means of control lines 84. The programmable controller 82 may also be used to controllably activate the compressor 64 and drying station 68 by way of respective control lines 86, 88. When at least one of the solenoid valves is open to permit dry gas flow to its associated supply line 22, the programmable controller can also be made to activate the compressor 64 and drying station 68. Those skilled in this art will appreciate that the controller 82 may be programmed to activate the compressor 64, drying station 68 and the solenoid valves 81 so as to achieve a desired time duration and time schedule of dry gas purging to any given number of prestressing cables 12. A suitable controller for implementing a dry gas purging program without feedback and automatic control is the micro programmable controller distributed by IDEC Izumi Corp. of Vancouver, British Columbia, Canada under model designation MICRO-1. A controller more suitable for a dry gas purging system with feedback of moisture content in the cable sheaths and automatic control of dry gas flow rate in the supply lines is described below.

Any known ambient temperature override means 90 may be used if desired to disable the controller and shut down the system when the ambient air temperature in the concrete structure falls below a given temperature, for instance $-10°$ C. This is to avoid unnecessary production and supply of dried air when any moisture present in the prestressing cables 12 will likely be in a frozen state. Another override means for the controller may involve monitoring of the moisture content of the dry gas in the main supply line 70 by means of an in-line relative humidity and temperature sensor 95. This temperature and relative humidity data is conveyed to the controller 82 by means of data line 97. A system shut-down can then be effected by the controller should the moisture content of the dry gas exceed a desired maximum. The system shut-down may be achieved by automatically deactivating the compressor 64 and drying station 68. Alternatively, by employing an automatic regulator valve for regulator valve 72, the controller 82 may also be used to close the valve 72 by means of control line 96 when the moisture content in the feed line exceeds a preselected level. This would prevent pressurizing the prestressing elements with a moist gas in the event of failure of the compressor 64 or of the drying station 68.

The individual supply lines 22 may also be provided with relative humidity and temperature sensors 95A which convey their data through data lines 97A to the controller. In the event of an excessive moisture content in any of the lines, the controller can be made to shut off the appropriate solenoid valve 81. An excessive moisture content may be detected in one of the supply lines 22 but not in the main supply line 70 if, for instance, there is a leak in one of the supply lines.

The gas pressure sensors 80 in each supply line may also convey pressure data to the controller 82 by data lines 98. In this manner, the controller can be employed to monitor the pressures in the supply lines 22 so that they do not exceed the capacity of the supply lines or the branch lines 23, nor the capacity of the drying station 68. The pressure of the supply lines may be reduced in such cases by automatic control of the regulators 76 in each individual supply line by means of control lines 77, or by automatic control of the regulator 72 in the main supply line 70 by means of control line 96.

The programmable controller means 82 may also be associated with any suitable display and control panel 92 to facilitate its operation. A recording system (not shown) may also be associated with the controller so as to record the various items of data received by the controller over the data lines of the system 62 and also to record the control activities undertaken during the course of pressurization through the control lines of the system.

Figure 10:
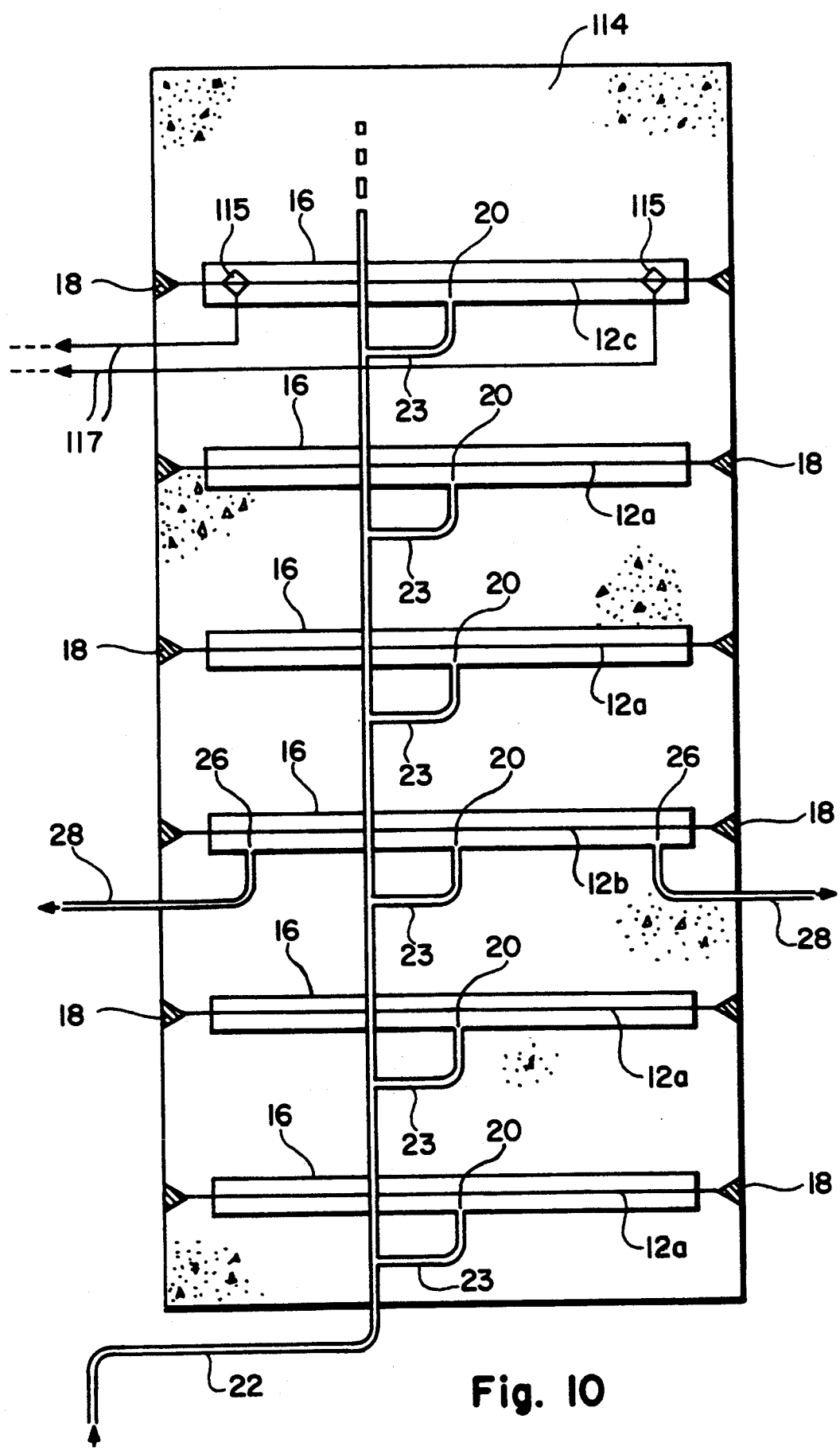
FIG. 10 is a schematic representation of an arrangement for the protection of an array of prestressing elements in a slab section of a post-tension concrete structure using the configurations of FIGS. 7 and 8, and suitable for use with the gas supply and control means of FIG. 9.

A typical configuration for the drying, protection and monitoring of an array of prestressing elements 12a, 12b and 12c in a slab section 114 of a post-tension concrete structure is shown in FIG. 10. The dry gas supply line 22 for the cables 12a, 12b and 12c may be connected to the programmable site-manufactured dry gas supply of FIG. 9.

The prestressing cables 12a have the single inlet port configuration previously explained in relation to FIG. 8. The cables 12b and 12c are control cables for monitoring the progress and effectiveness of drying and protection of the cables in the array. In a control cable 12b, an outlet port 26 is provided at one or at each of the terminal ends of the cable as explained in relation to the port configuration illustrated by FIG. 7. To the outlet ports may be attached gas discharge lines 28 for sampling and measurement. Alternatively, in the control cable 12c, an embedded humidity measurement means, such as a temperature and relative humidity sensor, may be provided at each end of the cable as shown schematically at 115 in order to determine the moisture content of the gaseous environments within the sheath thereof. The control cable 12c will have the same configuration as the control cable 12b, the embedded probes being introduced through the outlet ports thereof as previously explained.

Periodic pressurization of the cable sheaths 16 in the prestressing array as shown in FIG. 10 may be undertaken with site-manufactured dry gas according to a preselected time schedule, with each dry gas purging cycle having a selected time duration of pressurization. By monitoring the moisture content of the gaseous environments in the control cables 12b or 12c during the course of periodic pressurization, it will be possible to revise the gas flow rate, time duration and schedule or frequency of pressurization to achieve or maintain a desired degree of drying in the cable sheaths. For instance, a certain duration and schedule of dry gas pressurization cycles may not in a given installation cause the gaseous environments in the cable sheaths to achieve or maintain a desired maximum moisture content between pressurization cycles. This may be due, for instance, to the cables having poor sealing to the outside atmosphere, such that cable sheath environments which are relatively dry immediately following a pressurization cycle may thereafter quickly reacquire high moisture levels.

The periodic sampling and measurement of the cable sheath gaseous environments for moisture content will therefore provide information to enable the duration, frequency or flow rate of dry gas purging to be increased to thereby maintain the desired levels of moisture content in the cable sheath environments and maintain such levels between purging cycles.

Where fully automatic control of periodic pressurization is desired, the moisture content measurement probes 115 of the control cables 12c are connected through data lines 117 to the programmable controller of FIG. 9. The solenoid valves 81 are actuated as required by the controller to maintain a pre-programmed maximum humidity value in each sheath 16 as measured by the probes 115. The controller will compare the measured humidity in the cable sheaths to the predetermined maximum value and take the necessary corrective action as described above to maintain the desired humidity levels in the sheaths. By way of data lines 118 from the flow meters 78, the controller may also be employed to monitor the flow rates in each supply line 22 and then adjust the regulators 76 to provide a flow rate in each of the supply lines so as to maintain the said moisture content as aforesaid. The flow meter or sensor 74 in the main supply line 70 may also be connected to the controller by means of a data line (not shown) for monitoring and control of the flow rate in the main supply line, if desired. A controller suitable for the fully automatic control of pressurization based on moisture content is distributed by ATI Automation Technology Inc. of Edina, Minn., U.S.A. under model XL 470.

The person skilled in this field of art will appreciate that various modifications of detail may be made to the preferred embodiments described above, all of which would come within the spirit and scope of the prevent invention.

What I claim as my invention is as follows:

1. An on-site method for the corrosion condition evaluation of unbonded prestressing elements in post-tension concrete structures in service, said elements each being disposed within a respective conduit means, said conduit means containing a gaseous environment to which said elements are subjected, the method comprising the steps of:
(a) locating said prestressing element within said concrete structure;
(b) providing at least two openings in said concrete structure at respective positions along the longitudinal length of said prestressing element and between terminal ends thereof, one of said openings being an inlet port and the other of said openings being an outlet port, the said ports each permitting communication with said gaseous environment in said conduit means;
(c) accessing said gaseous environment through said outlet port by extracting a sample of gas from said environment through said outlet port;
(d) measuring said gaseous environment sample accessed through said outlet port to determine its humidity; and
(e) correlating said humidity of said gaseous environment sample to the corrosion condition of said prestressing element between said inlet port and said outlet port.

2. The method according to claim 1, further including the steps of providing a source of dry non-corrosive gas in communication with said inlet port and subjecting said gaseous environment within the conduit means to said source of dry gas at a pressure and for a time sufficient to extract a sample of said gaseous environment through said outlet port for measuring said sample for humidity.

3. The method according to claim 2, wherein successive samples of said gaseous environment are extracted through said outlet port at predetermined time intervals, each such sample being measured to determine its humidity.

4. The method according to claim 3, wherein said successive samples are each extracted at a substantially constant flow rate.

5. The method according to claim 2, wherein said gaseous environment sample is measured to determine its specific humidity, and further including the step of deriving, from said specific humidity, the relative humidity of said sample at selected temperatures.

6. The method according to claim 5, wherein said specific humidity is determined by measuring both temperature and relative humidity of said sample.

7. The method according to claim 6, wherein said source of dry gas is dry pressurized $N_2$.

8. The method according to claim 6, wherein said source of dry gas is dried ambient air.

9. The method according to claim 8, wherein said source of dry gas is ambient air dried to a humidity having a dew point of below approximately 5° C.

10. The method according to claim 9, wherein said source of dry gas is ambient air dried to a humidity having a dew point of below approximately −40° C.

11. The method according to claim 10, further comprising the step of analyzing said sample from said gaseous environment for determining concentration of a constituent gaseous component of said environment.

12. The method according to claim 11, wherein the said gaseous environment is analyzed for the concentration of a gaseous component selected from the group comprising: oxygen, carbon dioxide and hydrogen.

13. The method according to claim 2, wherein said outlet port is a first outlet port and wherein an additional said opening is provided in the concrete which constitutes a second outlet port, said first and second outlet ports respectively being located at opposite ends of the prestressing element adjacent end anchorages thereof, and said inlet port being substantially centrally located between said first outlet port and said second outlet port.

14. An apparatus for the on-site corrosion condition evaluation of unbonded prestressing elements in post-tension concrete structures in service, said elements each being disposed within a respective conduit means, said conduit means containing a gaseous environment to which said elements are subjected, the apparatus comprising:
(a) a supply means for supplying a dry non-corrosive gas;
(b) at least one inlet port and at least one outlet port, each port being provided in said concrete structure at respective positions along the longitudinal length of a said prestressing element and between terminal ends thereof, said ports each permitting communication with said gaseous environment in said conduit means;
(c) means for sampling and measurement of said gaseous environment to determine the humidity thereof;
(d) a regulator means to regulate pressure and flow rate of said dry gas; and
whereby said gaseous environment within the conduit means is subjected to a flow of said dry gas from said supply means and through said inlet port, said regulator means being adjusted to provide said flow of dry gas at a pressure and for a time sufficient to extract a sample of said gaseous environment through said outlet port to said means for sampling and measurement to determine the humidity of said sample.

15. The apparatus according to claim 14, wherein said supply means consists of a pressurized canister of said dry non-corrosive gas.

16. The apparatus according to claim 15, wherein said dry non-corrosive gas is $N_2$.

17. The apparatus according to claim 14, wherein said apparatus further includes a dry gas supply line, said supply line being connected at one end thereof to said supply means and at another end thereof to said inlet port, and wherein said regulator means is provided on said supply line.

18. The apparatus according to claim 17, wherein said regulator means comprises a regulator valve, a flowmeter and a pressure gauge.

19. The apparatus according to claim 14, wherein said apparatus further includes a portion of said concrete structure and wherein said inlet port is a cavity excavated into a surface of said portion of said concrete structure to thereby expose a portion of said prestressing element for visual inspection thereof, said cavity being sealed substantially airtight by a removable cover means secured to said surface, said cover means having an opening therein to admit said dry gas therethrough.

20. The apparatus according to claim 14, wherein said apparatus further includes a portion of said concrete structure and a gas discharge line, said discharge line being connected at one end thereof to said outlet port and at another end thereof to said means for sampling and measurement, and wherein said outlet port is a bore provided through a surface of said portion of said concrete structure, said bore having a valve means therein for connection to said gas discharge line.

21. The apparatus according to claim 14, wherein said apparatus further includes a portion of said concrete structure and a dry gas supply line, said dry gas supply line being connected at one end thereof to said supply means and at another end thereof to said inlet port, and wherein said inlet port is a bore provided through a surface of said portion of said concrete structure, said bore having a valve means therein for connection to said gas supply line.

22. The apparatus according to claim 14, wherein two outlet ports are provided, each being respectively located at opposite ends of said conduit means adjacent end anchorages thereof, said inlet port being located substantially centrally between said two outlet ports.

23. The apparatus according to claim 14, wherein said dry non-corrosive gas is dried ambient air.

24. The apparatus according to claim 23, wherein said supply means constitutes means for supplying ambient air dried to a humidity having a dew point of below approximately 5° C.

25. The apparatus according to claim 24, wherein said supply means constitutes means for supplying ambient air dried to a humidity having a dew point of below approximately −40° C.

26. The apparatus according to claim 25, wherein said supply means comprises:
(a) a compressor means for compressing ambient air; and
(b) a dryer means for drying said air compressed by said compressor means and for supplying dried air to said conduit means.

27. The apparatus according to claim 26, wherein said compressor means is a rotary screw-type compressor, and wherein said dryer means is a heatless regenerating desiccant dryer.

28. The apparatus according to claim 14, wherein said means for sampling and measurement comprises:
(a) a flow control means for controlling the flow rate of said sample of gaseous environment extracted through said outlet port;
(b) a sampling chamber for receiving said sample of gaseous environment; and
(c) a meter means for measuring the relative humidity and temperature of said sample, said meter means having a measurement probe extending into said sampling chamber.

29. The apparatus according to claim 28, wherein said sampling chamber comprises:
(a) an inlet tube for said sample of gaseous environment, said inlet tube having an open end extending into the chamber;
(b) an exhaust port for venting said chamber to outside atmosphere;
and wherein said measurement probe is positioned with a terminal end thereof located within said chamber and between said open end of said inlet tube and said exhaust port of said chamber.

30. An on-site method for the corrosion protection of unbonded prestressing elements in a post-tension concrete structure in service, said elements each being disposed within a respective conduit means, said conduit means each containing a gaseous environment to which said elements are subjected, the method comprising the steps of:
(a) locating a plurality of said post-tension prestressing elements within said concrete structure;
(b) providing at least one inlet port in said concrete structure for each of said prestressing elements, said inlet ports being located at respective positions along the longitudinal lengths of said prestressing elements and between terminal ends thereof, the said inlet ports respectively permitting communication with said gaseous environments in said conduit means;
(c) providing a source of dry non-corrosive gas in communication with said inlet ports;
(d) subjecting said gaseous environments in said conduit means to said source of dry gas so as to cyclically pressurize each of said conduit means according to a selected time schedule with said dry gas at a selected flow rate thereof and for a selected time duration of pressurization;
(e) periodically accessing the gaseous environments of a preselected number of said prestressing elements for measurement of said gaseous environments to determine the humidity thereof;
(f) comparing said measured humidity with a predetermined maximum humidity value; and
(g) adjusting said flow rate, said time duration and said time schedule of cyclic pressurization so as to maintain said predetermined maximum humidity value in the gaseous environments of each of said preselected number of prestressing elements between cycles of pressurization.

31. The method according to claim 30, wherein said measured humidity is determined by measuring both temperature and relative humidity of said sample.

32. The method according to claim 30, wherein said source of dry gas is site-manufactured dried ambient air.

33. The method according to claim 32, wherein said source of site-manufactured dry gas is ambient air dried to a humidity having a dew point of below approximately 5° C.

34. The method according to claim 33, wherein said source of site-manufactured dry gas is ambient air dried to a humidity having a dew point of below approximately −40° C.

35. The method according to claim 30, wherein said gaseous environments of said preselected number of prestressing elements are accessed at locations substantially adjacent the terminal ends of each of said preselected number of prestressing elements and said inlet ports are located substantially centrally along the length of said same elements.

36. An on-site method for the corrosion condition evaluation of unbonded prestressing elements in post-tension concrete structures in service, said elements each being disposed within a respective conduit, said conduit containing a gaseous environment to which said elements are subjected, the method comprising the steps of:
(a) locating said prestressing element within said concrete structure;
(b) providing at least two openings in said concrete structure at respective positions along the longitudinal length of said prestressing element and between terminal ends thereof, one of said openings being an inlet port and the other of said openings being an outlet port, the said ports each permitting communication with said gaseous environment in said conduit;
(c) accessing said gaseous environment through said outlet port by extracting a sample of gas from said environment through said outlet port;

(d) measuring said gaseous environment sample accessed through said outlet port to determine humidity of said gaseous environment sample; and (e) correlating said humidity of said gaseous environment sample to the corrosion condition of said prestressing element between said inlet port and said outlet port.

37. The method according to claim 36, further including the steps of providing a source of dry non-corrosive gas in communication with said inlet port and subjecting said gaseous environment within the conduit to said source of dry gas at a pressure and for a time sufficient to extract a sample of said gaseous environment through said outlet port for measuring said sample for humidity.

38. The method according to claim 37, wherein successive samples of said gaseous environment are extracted through said outlet port at predetermined time intervals, each such sample being measured to determine its humidity.

39. The method according to claim 38, wherein said successive samples are each extracted at a substantially constant flow rate.

40. The method according to claim 37, wherein said gaseous environment sample is measured to determine its specific humidity, and further including the step of deriving, from said specific humidity, the relative humidity of said sample at selected temperatures.

41. The method according to claim 40, wherein said specific humidity is determined by measuring both temperature and relative humidity of said sample.

42. The method according to claim 41, wherein said source of dry gas is dry pressurized $N_2$.

43. The method according to claim 41, wherein said source of dry gas is dried ambient air.

44. The method according to claim 43, wherein said source of dry gas is ambient air dried to a humidity having a dew point of below approximately 5° C.

45. The method according to claim 44, wherein said source of dry gas is ambient air dried to a humidity having a dew point of below approximately −40° C.

46. The method according to claim 45, further comprising the step of analyzing said sample from said gaseous environment for determining concentration of a constituent gaseous component of said environment.

47. The method according to claim 46, wherein the said gaseous environment is analyzed for the concentration of a gaseous component selected from the group comprising: oxygen, carbon dioxide and hydrogen.

48. The method according to claim 37, wherein said outlet port is a first outlet port and wherein an additional said opening is provided in the concrete which constitutes a second outlet port, said first and second outlet ports respectively being located at opposite ends of the prestressing element adjacent end anchorages thereof, and said inlet port being substantially centrally located between said first outlet port and said second outlet port.

49. An apparatus for the on-site corrosion condition evaluation of unbonded prestressing elements in post-tension concrete structures in service, said elements each being disposed within a respective conduit, said conduit containing a gaseous environment to which said elements are subjected, the apparatus comprising:

(a) a supply for supplying a dry non-corrosive gas;

(b) at least one inlet port and at least one outlet port, each port being provided in said concrete structure at respective positions along the longitudinal length of a said prestressing element and between terminal ends thereof, said ports each permitting communication with said gaseous environment in said conduit;

(c) a sampler for sampling and measurement of said gaseous environment to determine the humidity thereof;

(d) a regulator to regulate pressure and flow rate of said dry gas; and whereby said gaseous environment within the conduit is subjected to a flow of said dry gas from said supply and through said inlet port, said regulator being adjusted to provide said flow of dry gas at a pressure and for a time sufficient to extract a sample of said gaseous environment through said outlet port to said sampler for sampling and measurement to determine the humidity of said sample.

50. The apparatus according to claim 49, wherein said supply consists of a pressurized canister of said dry non-corrosive gas.

51. The apparatus according to claim 50, wherein said dry non-corrosive gas is $N_2$.

52. The apparatus according to claim 49, wherein said apparatus further includes a dry gas supply line, said supply line being connected at one end thereof to said supply and at another end thereof to said inlet port, and wherein said regulator is provided on said supply line.

53. The apparatus according to claim 52, wherein said regulator comprises a regulator valve, a flowmeter and a pressure gauge.

54. The apparatus according to claim 49, wherein said inlet port is a cavity excavated into a surface of said concrete structure to thereby expose a portion of said prestressing element for visual inspection thereof, said cavity being sealed substantially airtight by a removable cover secured to said surface, said cover having an opening therein to admit said dry gas therethrough.

55. The apparatus according to claim 49, wherein said apparatus further includes a portion of said concrete structure and a gas discharge line, said discharge line being connected at one end thereof to said outlet port and at another end thereof to said sampler, and wherein said outlet port is a bore provided through a surface of said portion of said concrete structure, said bore having a valve therein for connection to said gas discharge line.

56. The apparatus according to claim 49, wherein said apparatus further includes a portion of said concrete structure and a dry gas supply line, said dry gas supply line being connected at one end thereof to said supply and at another end thereof to said inlet port, and wherein said inlet port is a bore provided through a surface of said portion concrete structure, said bore having a valve therein for connection to said gas supply line.

57. The apparatus according to claim 49, wherein two outlet ports are provided, each being respectively located at opposite ends of said conduit adjacent end anchorages thereof, said inlet port being located substantially centrally between said two outlet ports.

58. The apparatus according to claim 49, wherein said dry non-corrosive gas is dried ambient air.

59. The apparatus according to claim 58, wherein said supply supplies ambient air dried to a humidity having a dew point of below approximately 5° C.

60. The apparatus according to claim 59, wherein said supply supplies ambient air dried to a humidity having a dew point of below approximately −40° C.

61. The apparatus according to claim 60, wherein said supply comprises:

(a) a compressor for compressing ambient air; and
(b) a dryer for drying said air compressed by said compressor and for supplying dried air to said conduit.

62. The apparatus according to claim 61, wherein said compressor is a rotary screw-type compressor, and wherein said dryer is a heatless regenerating desiccant dryer.

63. The apparatus according to claim 49, wherein said comprises:
(a) a flow control for controlling the flow rate of said sample of gaseous environment extracted through said outlet port;
(b) a sampling chamber for receiving said sample of gaseous environment; and
(c) meter for measuring the relative humidity and temperature of said sample, said meter having a measurement probe extending into said sampling chamber.

64. The apparatus according to claim 63, wherein said sampling chamber comprises:
(a) an inlet tube for said sample of gaseous environment, said inlet tube having an open end extending into the chamber;
(b) an exhaust port for venting said chamber to outside atmosphere;
and wherein said measurement probe is positioned with a terminal end thereof located within said chamber and between said open end of said inlet tube and said exhaust port of said chamber.

* * * * *